United States Patent [19]

Schmidt et al.

[11] 4,128,718
[45] Dec. 5, 1978

[54] HYDROXYPHENYLATED HYDANTOINS

[75] Inventors: Andreas Schmidt, Reinach, Switzerland; Janet B. Peterson, Yonkers; Martin Dexter, Briarcliff Manor, both of N.Y.

[73] Assignee: Ciba-Geigy Corporation, Ardsley, N.Y.

[21] Appl. No.: 778,654

[22] Filed: Mar. 17, 1977

Related U.S. Application Data

[60] Division of Ser. No. 614,039, Sep. 17, 1975, Pat. No. 4,044,019, which is a division of Ser. No. 469,717, May 14, 1974, Pat. No. 3,939,175, which is a continuation-in-part of Ser. No. 357,744, May 7, 1973, abandoned.

[51] Int. Cl.$^2$ .................. C07D 233/78; C07D 235/02
[52] U.S. Cl. ............................................... 548/313
[58] Field of Search ........................................ 548/313

[56] References Cited

U.S. PATENT DOCUMENTS

| | | | |
|---|---|---|---|
| 3,939,175 | 2/1976 | Schmidt et al. | 548/313 |
| 4,044,019 | 8/1977 | Schmidt et al. | 548/313 |

*Primary Examiner*—Richard L. Raymond
*Attorney, Agent, or Firm*—Luther A. R. Hall

[57] ABSTRACT

New hydroxyphenylated hydantoins are useful as stabilizers for synthetic organic polymeric materials. The new hydroxyphenylated hydantoins may be additionally substituted in the 1,3 and/or 5 positions of the hydantoin ring.

The hydroxyphenylated and 5-substituted hydroxyphenylated hydantoins are generally prepared by reacting hydroxphenylated ketones or aldehydes with alkali cyanide and ammonium carbonate. Hydroxyphenylated hydantoins substituted in the 1 and/or 3 positions are generally prepared by reacting the 1 and/or 3-unsubstituted hydroxyphenylated hydantoins with the corresponding halogen or dialkylaminomethyl derivatives.

6 Claims, No Drawings

HYDROXYPHENYLATED HYDANTOINS

The present application is a divisional of application, Ser. No. 614,039, filed Sept. 17, 1975, now U.S. Pat. No. 4,044,019, issued Aug. 23, 1977, which in turn is a divisional of application, Ser. No. 469,717, filed May 14, 1974, now U.S. Pat. No. 3,939,175, issued Feb. 17, 1976, which in turn is a continuation-in-part of application, Ser. No. 357,744, filed May 7, 1973, now abandoned.

The present invention pertains to bis and tris hindered hydroxyphenylated hydantoins of the general formula

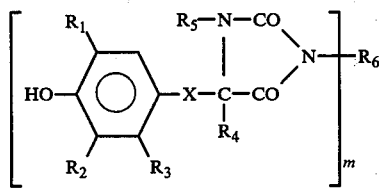

which are useful as stabilizers for organic materials for which the essential material constituting a disclosure thereof is incorporated by reference from Ser. No. 469,717, filed May 14, 1974, now U.S. Pat. No. 3,939,175.

We claim:

1. A compound of the formula

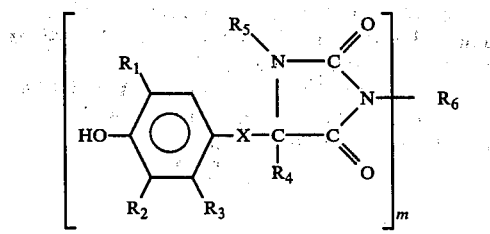

wherein $R_1$ denotes alkyl with 1 to 8 carbon atoms, cycloalkyl with 6 to 8 carbon atoms or aralkyl with 7 to 9 carbon atoms; $R_2$ denotes hydrogen, alkyl with 1 to 8 carbon atoms, cycloalkyl with 6 to 8 carbon atoms or aralkyl with 7 to 9 carbon atoms; $R_3$ denotes hydrogen or methyl; X denotes a direct bond, alkylene with 1 to 18 carbon atoms, which can be interrupted by oxygen or sulphur atoms, or the radical —O—CH$_2$—, wherein the oxygen atoms is bonded to the phenol radical; $R_4$ denotes hydrogen, alkyl with 1 to 17 carbon atoms, alkenyl with 2 to 17 carbon atoms, thiaalkyl with 3 to 21 carbon atoms, oxaalkyl with 3 to 21 carbon atoms, cyclohexyl, benzyl, phenyl, alkylphenyl with 7 to 14 carbon atoms, alkoxyphenyl with 7 to 24 carbon atoms, chlorophenyl, dichlorophenyl, naphthyl or a group

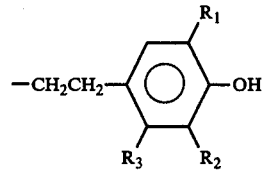

or X and $R_4$ conjointly with the carbon atom in the 5-position of the hydantoin ring denote one of the radicals

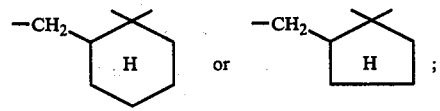

$R_5$ denotes hydrogen, alkyl with 1 to 18 carbon atoms, alkenyl with 3 to 18 carbon atoms, cyclohexyl, benzyl or hydroxybenzyl which is unsubstituted or substituted by 1 to 3 alkyl groups each with 1 to 4 carbon atoms; m denotes 2, and $R_6$ denotes alkylene with 1 to 18 carbon atoms, oxaalkylene with 4 to 21 carbon atoms, wherein the carbon atom bonded to the nitrogen does not carry any further hetero-atoms, thiaalkylene with 4 to 21 carbon atoms, wherein the carbon atom bonded to nitrogen carries no further hetero-atoms, or one of the groups

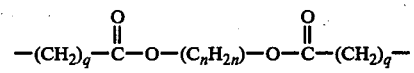

wherein q is 1 or 2 and n is 2 to 18,

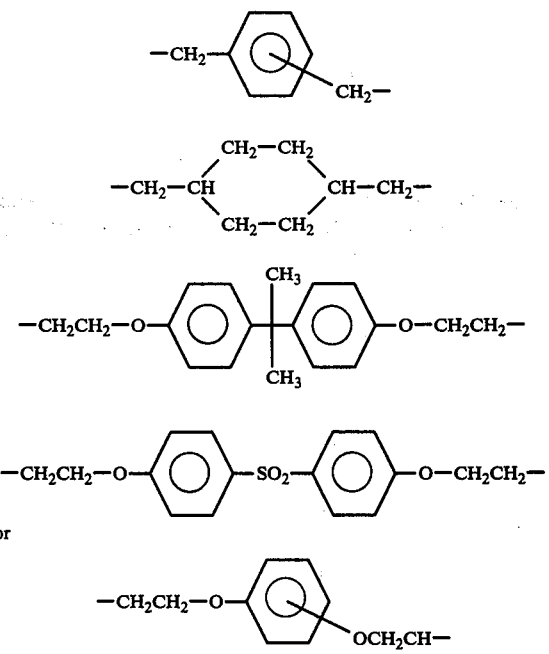

2. A compound according to claim 1, wherein $R_1$ denotes alkyl with 1 to 4 carbon atoms or cycloalkyl with 6 to 8 carbon atoms; $R_2$ denotes hydrogen, alkyl with 1 to 4 carbon atoms or cycloalkyl with 6 to 8 carbon atoms; $R_3$ denotes hydrogen; X denotes one of the radicals

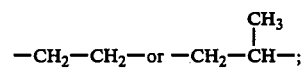

$R_4$ denotes alkyl with 1 to 17 carbon atoms, cyclohexyl, benzyl, phenyl or a group

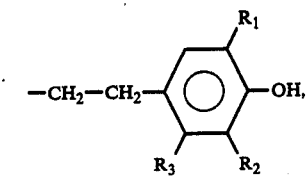

$R_5$ denotes hydrogen, alkyl with 1 to 18 carbon atoms or hydroxybenzyl substituted by 1 to 3 alkyl groups each having 1 to 4 carbon atoms; $R_6$ denotes alkylene with 1 to 18 carbon atoms or the group $-CH_2CH_2-O-CH_2CH_2-$.

3. A compound according to claim 1, of the formula

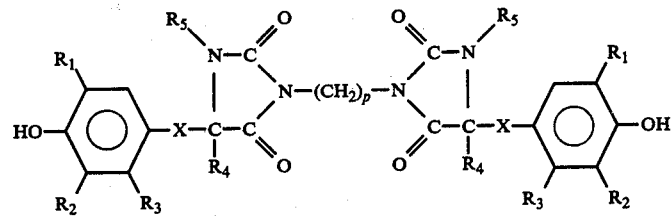

wherein $R_1$ and $R_2$ independently of one another denote alkyl with 1 to 4 carbon atoms; $R_3$ denotes hydrogen; X denotes a direct bond, $$-CH_2-CH_2-\text{ or }-CH_2-\overset{CH_3}{\underset{}{CH}}-;$$

$R_4$ denotes alkyl with 1 to 17 carbon atoms or the group

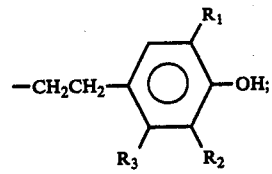

$R_5$ denotes hydrogen or alkyl with 1 to 18 carbon atoms and p denotes 1 to 18.

4. A compound according to claim 1 which is 3,3'-methylene-bis-[5-(3'',5''-di-tert-butyl-4''-hydroxyphenylethyl)-5-methylhydantoin].

5. A compound according to claim 1 which is 3,3'-hexamethylene-bis-[5-(3'',5''-di-tert-butyl-4''-hydroxyphenylethyl)-5-methylhydantoin].

6. A compound according to claim 1 which is 3,3'-oxydiethylene-bis-[5-(3'',5''-di-tert-butyl-4''-hydroxyphenylethyl)-5-methylhydantoin].